United States Patent [19]
Tropsha et al.

[11] Patent Number: 5,654,054
[45] Date of Patent: Aug. 5, 1997

[54] BARRIER COATING

[75] Inventors: Yelena G. Tropsha, Chapel Hill; Richard P. Clarke; Mitchell K. Antoon, both of Raleigh, all of N.C.

[73] Assignee: Becton, Dickinson and Company, Franklin Lakes, N.J.

[21] Appl. No.: 423,172

[22] Filed: Apr. 18, 1995

Related U.S. Application Data

[63] Continuation-in-part of Ser. No. 993,275, Dec. 18, 1992, abandoned.

[51] Int. Cl.$^6$ .................................................. A61B 5/00
[52] U.S. Cl. ................ 428/36.6; 428/34.6; 428/36.7; 428/702; 206/524.2; 220/415; 220/456; 220/457; 604/226; 604/403; 128/771; 128/764
[58] Field of Search ..................... 428/35.7, 34.1, 428/34.4, 34.6, 36.7, 702; 206/524.2; 220/415, 456, 457; 604/226, 403; 128/771, 764; 422/102, 99, 58

[56] References Cited

U.S. PATENT DOCUMENTS

| | | | |
|---|---|---|---|
| 4,131,200 | 12/1978 | Rinfret | 206/484 |
| 5,297,561 | 3/1994 | Hulon | 128/764 |

*Primary Examiner*—Charles Nold
*Attorney, Agent, or Firm*—Nanette S. Thomas

[57] ABSTRACT

The present invention is a plastic container coated with a barrier coating. The barrier coating is useful for providing an effective barrier against gas permeability in containers and for extending shelf-life of containers, especially plastic evacuated blood collection devices.

3 Claims, 2 Drawing Sheets

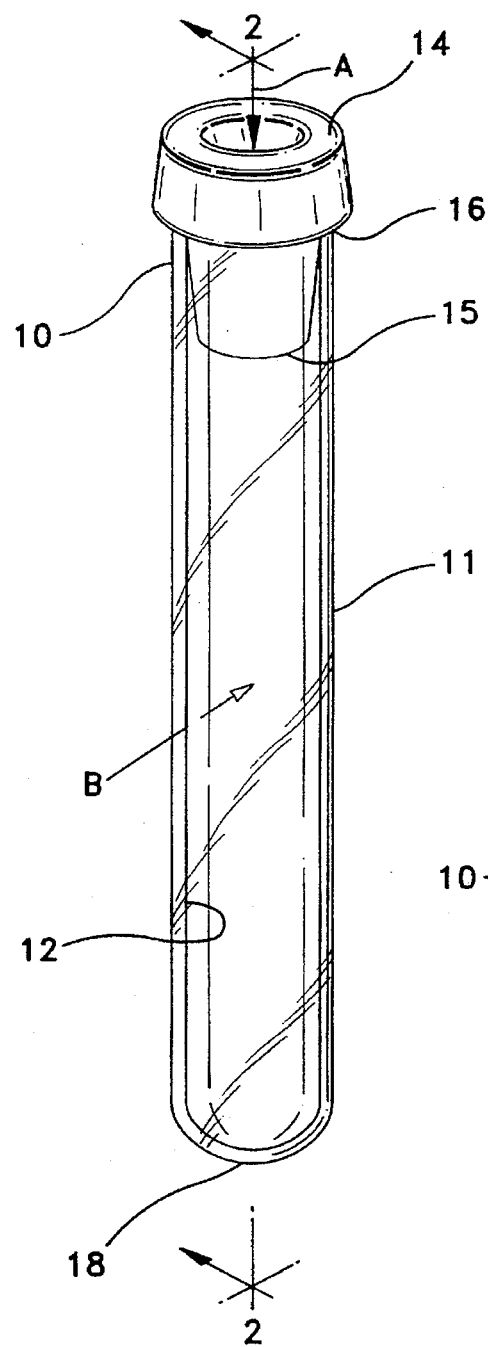
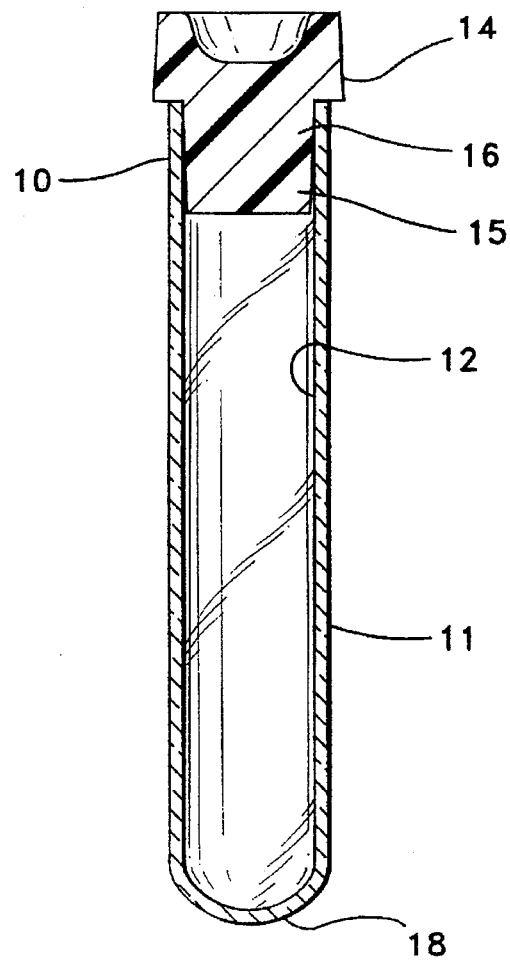

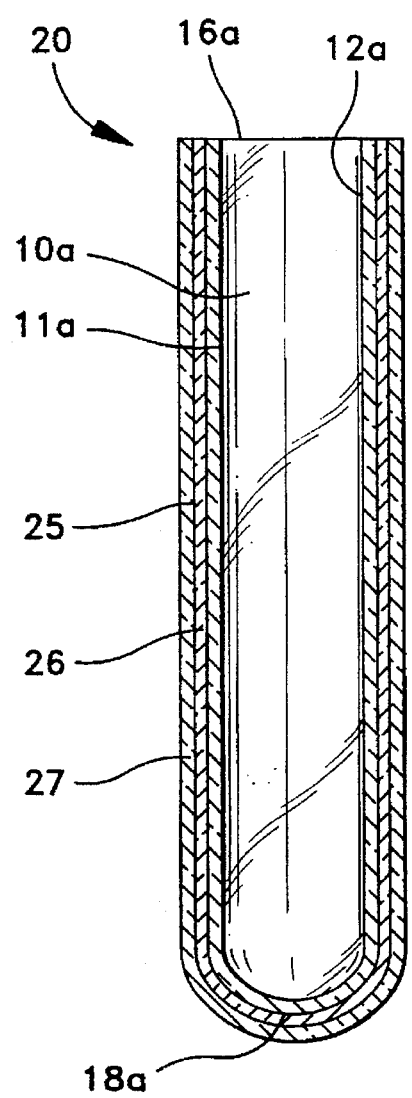
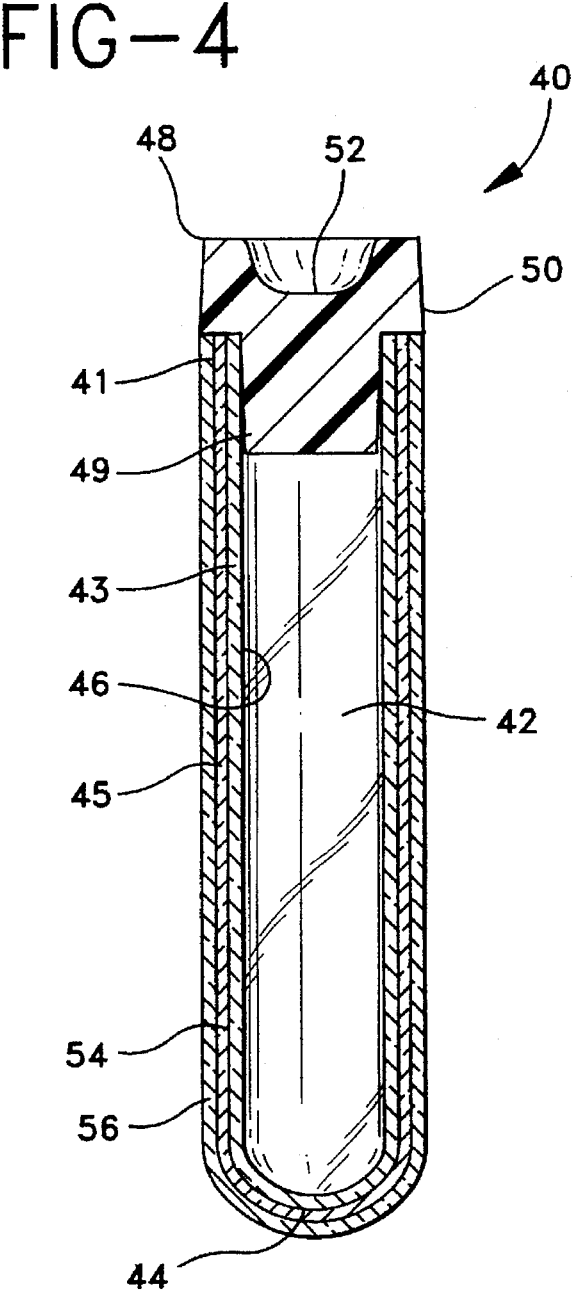

BARRIER COATING

BACKGROUND OF THE INVENTION

This application is a continuation-in-part of U.S. Ser. No. 07/993,275, filed on Dec. 18, 1992, now abandoned.

1. FIELD OF THE INVENTION

This invention relates to a barrier coating for providing an effective barrier against gas and water permeability for containers, especially plastic evacuated blood collection tubes.

2. DESCRIPTION OF THE RELATED ART

With the increased emphasis on the use of plastic medical products, a special need exists for improving the barrier properties of articles made of polymers.

Such medical products that would derive a considerable benefit from improving their barrier properties include, but are not limited to, collection tubes and particularly those used for blood collection.

Blood collection tubes require certain performance standards to be acceptable for use in medical applications. Such performance standards include the ability to maintain greater than about 90% original draw volume over a one year period, to be radiation sterilizable and to be non interfering in tests and analysis.

Therefore, a need exists to improve the barrier properties of articles made of polymers and in particular plastic evacuated blood collection tubes wherein certain performance standards would be able to be met and the article would be effective and is able in medical applications.

SUMMARY OF THE INVENTION

The present invention is a plastic composite container coated with a barrier coating comprising at least two barrier materials. Desirably, the barrier coating comprises a first layer of an inorganic material and a second layer of a polymer material.

The first layer of the barrier coating may preferably be an aluminum oxide based composition, such as AlOx wherein x is from 0.3 to about 0.9; a silicon oxide based composition; or a diamond based composition. Most preferably, the first layer is an aluminum oxide based composition.

The second layer may preferably be vinylidene chloride-acrylonitrile-methyl methacrylate-methyl acrylate-acrylic acid copolymers, thermosetting epoxy coatings, parylene polymers, or polyesters. The barrier coating may be formed either on an interior surface portion, on an exterior surface portion, or both of the container. Preferably, the second layer is a parylene polymer. Parylene is the generic name for members of a polymer series developed by Union Carbide Corporation. The base member of the series, called parylene N, is poly-p-xylylene, a linear, crystalline material:

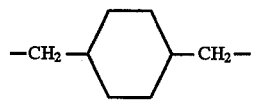

Parylene C, a second member of the parylene series is produced from the same monomer as parylene N and modified by the substitution of a chlorine atom for one of the aromatic hydrogens:

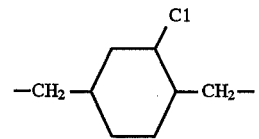

Parylene D, the third member of the parylene series is produced from the same monomer as parylene N and modified by the substitution of the chlorine atom for two of the aromatic hydrogens:

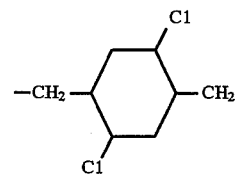

Most preferably, the polymer layer is a vinylidene chloride-methyl methacrylate-methacrylate acrylic acid polymer. This polymer is available as DARAN® 8600-C (trademark of W. R. Grace and Co.) sold by GRACE, Organic Chemicals Division, Lexington, Mass.

Plastic tubes coated with the barrier coating are able to maintain substantially far better vacuum retention and draw volume retention than previous tubes comprised of polymer compositions and blends thereof without a coating of barrier materials.

Printing may be placed on the barrier coating applied to the container of interest. For example, a product identification, bar code, brand name, company logo, lot number, expiration date and other data and information may all be included on the barrier coating.

Moreover, a matte finish or a corona discharged surface may be developed on the barrier coating so as to make the surface appropriate for writing additional information on the label. Furthermore, a pressure sensitive adhesive label may be placed over the barrier coating so as to accommodate various hospital over-labels, for example.

Optionally, the substrate may be pre-treated with a first plasma coating of oxygen, hydrogen, air or water vapor, followed by the depositing of silicon oxide or aluminum oxide. Most preferably, the first plasma coating is oxygen. It is believed that the pre-treatment provides for improved adherence qualities between the coating of silicon oxide or aluminum oxide and the article.

BRIEF DESCRIPTION OF THE DRAWINGS

FIG. 1 is a perspective view of a typical blood collection tube with a stopper.

FIG. 2 is a longitudinal sectional view of the tube of FIG. 1 taken along line 2—2.

FIG. 3 is a longitudinal sectional view of a tube-shaped container, similar to the tube of FIG. 1 without a stopper, comprising a barrier coating.

FIG. 4 is a longitudinal sectional view of a tube-shaped container, similar to the tube of FIG. 1 with a stopper, comprising a barrier coating.

DETAILED DESCRIPTION

Referring to the drawings in which like reference characters refer to like parts throughout the several views thereof, FIGS. 1 and 2 show a typical blood collection tube 10, having a sidewall 11 extending 30 from an open end 16 to a closed end 18 and stopper 14 which includes a lower annular portion or skirt 15 which extends into and presses against the inner surface 12 of the sidewall for maintaining stopper 14 in place.

FIG. 3 shows the preferred embodiment of the invention, a plastic tube coated with at least two layers of barrier materials. The preferred embodiment includes many components which are substantially identical to the components of FIGS. 1 and 2. Accordingly, similar components performing similar functions will be numbered identically to those components of FIGS. 1 and 2, except that a suffix "a" will be used to identify those components in FIG. 3.

Referring now to FIG. 3, the preferred embodiment of the invention, collection tube assembly 20 comprises a plastic tube 10a, having a sidewall 11a extending from an open end 16a to a closed end 18a. A barrier coating 25 extends over a substantial portion of the length of the tube which is upon the outer surface of the tube with the exception of open end 16a. Barrier coating 25 comprises a first layer 26 of an inorganic material and a second layer 27 of a polymer material.

FIG. 4 illustrates an alternate embodiment of the invention, wherein collection tube assembly 40 comprises stopper 48 in place for closing open end 41 of tube 42. As can be seen, sidewall 43 extends from open end 41 to closed end 44 and stopper 48 includes an annular upper portion 50 which extends over the top edge of tube 42. Stopper 48 includes a lower annular portion or skirt 49 which extends into and presses against the inside inner surface 46 of sidewall 43 for maintaining stopper 48 in place and a well 52.

Covering a substantial portion of the length of the tube is a barrier coating 45. Barrier coating 45 covers substantially most of the tube with the exception of open end 41 thereof. Barrier coating 45 comprises a first layer 54 of an inorganic material and a second layer 56 of a polymer material. FIG. 4 differs from the embodiment in FIG. 3 in that the tube may be evacuated with the simultaneous placement of stopper 48 therein after the application of barrier coating 45 over the tube. Alternatively, the barrier coating may be applied to the tube before it has been evacuated.

An alternate embodiment of the invention also includes a barrier coating incorporating both the upper portion of the stopper, as well as the entire container tube. Such an embodiment may be utilized, for example, for sealing the container with the stopper in place. Once a sample has been placed in the tube, the sample cannot be tampered with by removal of the stopper. Additionally, serrations could be included at the tube, stopper interface. The serrations may be registered so that it can be determined if the sealed container has been tampered with.

It will be understood by practitioners-in-the-art that such tubes may also contain reagents in the form of additives or coatings on the inner wall of the tube.

The barrier coating forms a substantially clear or translucent barrier. Therefore, the contents of a plastic tube layered with a barrier coating comprising at least two layers of barrier materials are substantially visible to the observer at the same time identifying information may be displayed over the barrier coating after it is applied to the plastic tube.

The inorganic material of the barrier coating may be formed on a substrate as a first layer by radio frequency discharge, direct or dual ion beam deposition, sputtering or plasma chemical vapor deposition, as described in U.S. Pat. Nos. 4,698,256, 4,809,876, 4,992,298 and 5,055,318, the disclosures of which are herein incorporated by reference.

The second layer of the barrier coating, a polymer material, may be a parylene polymer applied to the first layer by a process similar to vacuum metallizing, as described in U.S. Pat. Nos. 3,342,754 and 3,300,332, the disclosures of which are herein incorporated by reference. Alternatively, the second layer may be vinylidene chloride-acrylonitrile-methyl methacrylate-methyl acrylate-acid acrylic polymer, applied to the first layer by dip-coating, roll-coating or spraying an aqueous emulsion of the polymer, followed by air drying of the coating, as described in U.S. Pat. Nos. 5,093,194 and 4,497,859, the disclosure of which are herein incorporated by reference.

The barrier coating of the present invention is preferably a first layer material comprising aluminum oxide, and a second layer of vinylidene chloride-acrylonitrile-methyl methacrylate-methyl acrylate-acrylic acid polymer applied to the first layer. A plastic blood collection tube coated with the barrier coating will not interfere with testing and analysis that is typically performed on blood in a tube. Such tests include but are not limited to, routine chemical analysis, biological inertness, hematology, blood chemistry, blood typing, toxicology analysis or therapeutic drug monitoring and other clinical tests involving body fluids. Furthermore, a plastic blood collection tube coated with the barrier coating is capable of being subjected to automated machinery such as centrifuges and may be exposed to certain levels of radiation in the sterilization process with substantially no change in optical or mechanical and functional properties.

A plastic blood collection tube coated with the barrier coating is able to maintain 90% original draw volume over a period of one year. Draw volume retention depends on the existence of a partial vacuum, or reduced pressure, inside the tube. The draw volume changes in direct proportion to the change in vacuum (reduced pressure). Therefore, draw volume retention is dependent on good vacuum retention. A plastic tube coated with a barrier coating substantially prevents gas permeation through the tube material so as to maintain and enhance the vacuum retention and draw volume retention of the tube.

If the barrier coating is also coated or applied on the inner surface of the plastic blood collection tube, the barrier coating may be hemorepellent and/or have characteristics of a clot activator if the first layer of the barrier coating is a diamond composition.

It will be understood that it makes no difference whether the plastic composite container is evacuated or not evacuated in accordance with this invention. The presence of a barrier coating on the outer surface of the container has the effect of maintaining the general integrity of the container holding a sample so that it may be properly disposed of without any contamination to the user. Notable is the clarity of the barrier coating as coated or applied on the container and its abrasion and scratch resistance.

The barrier coating used in accordance with this disclosure, may contain conventional additives and ingredients which do not adversely affect the properties of articles made therefrom.

EXAMPLE 1

METHOD FOR COATING PLASTIC SUBSTRATES TUBES WITH MULTI-LAYER BARRIER COATING

A silicone oxide coating was applied to polypropylene tubes and films (substrates) as follows:

The substrate was cleaned with a mixture comprising equal parts of a micro detergent and de-ionized (DI) water solution. The substrate was rinsed thoroughly in DI water and allowed to air dry. The cleaned substrate was then stored in a vacuum oven at room temperature until it was to be coated.

The cleaned substrate was then attached to a holder which fits midway between the electrodes in the glass vacuum chamber. The chamber was closed and a mechanical pump was used to achieve a base pressure of 5 mTorr.

The electrode configuration is internally capacitively coupled with permanent magnets on the backside of the titanium electrodes. The special configuration provides the ability to confine the glow between the electrodes because of the increase in collision probability between electrons and reacting gas molecules. The net result of applying a magnetic field is similar to increasing the power applied to the electrodes, but without the disadvantages of higher bombardment energies and increased substrate heating. The use of magnetron discharge allows operation in the low pressure region and a substantial increase in polymer deposition rate.

The monomer which consists of a mixture of trimethylsilane (TMS) and oxygen was introduced through stainless steel tubing near the electrodes. The gases were mixed in the monomer inlet line before introduction into the chamber. Flow rates were manually controlled by stainless steel metering valves. A power supply operating at an audio frequency of 40 kHz was used to supply power to the electrodes. The system parameters used for thin film deposition of plasma polymerized TMS/$O_2$ on the polymer substrate were as follows:

| Surface Pretreatment: | Base Pressure | = | 5m Torr |
| --- | --- | --- | --- |
| | Oxygen Flow | = | 10 sccm |
| | System Pressure | = | 140m Torr |
| | Power | = | 50 watts |
| | Time | = | 2 minutes |
| Oxide Deposition: | TMS Flow | = | 0.75–1.0 sccm |
| | Oxygen Flow | = | 2.5 = 3.0 sccm |
| | System Pressure | = | 90–100 mTorr |
| | Power | = | 30 watts |
| | Deposition Time | = | 5 minutes |

After the thin film was deposited, the reactor was allowed to cool. The reactor was then opened, and the substrate with a coating of silicon oxide was removed. The coated substrate was then subjected to a further coating of vinylidene chloride-acrylonitrile-methyl methacrylate-methyl acrylate-acrylic acid polymer (PVDC) as described in U.S. Pat. Nos. 5,093,194 and 4,497,859.

EXAMPLE 2

COMPARISON OF SUBSTRATES WITH AND WITHOUT MULTI-LAYER BARRIER COATINGS

All of the substrates prepared in accordance with Example 1 above were evaluated for oxygen permeance (OTR) as follows:

Film or plaque samples were tested for oxygen permeance (OTR) using a MO CON Ox-TRAN 2/20 (sold by Modem Controls, Inc.). A single side of the film sample was exposed to 1 atm of 100% oxygen atmosphere. Oxygen permeating through the sample film was entrained in a nitrogen carrier gas stream on the opposite side of the film, and detected by a coulmetric sensor. An electrical signal was produced in proportion to the amount of oxygen permeating through the sample. Samples were tested at 30° C. and 0% relative humidity (R. H.). Samples were conditioned for 1 to 20 hours prior to determining oxygen permeance. The results are reported in Table 1 in units of cc/m2-atm-day.

Tube samples were tested for oxygen permeance (OTR) using a MOCON Ox-TRAN 1,000 (sold by Modem Controls, Inc.). A package adapter was used for mounting the tubes in a manner that allowed the outside of the tube to be immersed in a 100% $O_2$ atmosphere while the inside of tube is flushed with a nitrogen carrier gas. The tubes were then tested at 20° C. and 50% R. H. The tubes were allowed to equilibrate for 2–14 days before a steady state permeability is determined. The results are reported in Table 1 in units of cc/$m^2$-atm-day.

TABLE 1

| Sample | $O_2$ Plasma Pretreatment | FIRST Coating | SECOND Coating | Oxygen Transmission Rate (cc/$m^2$-atm-day) (25° C.) |
| --- | --- | --- | --- | --- |
| PP film, control | no | $SiO_x$ | no | 46–59 |
| PP film | yes | $SiO_x$ | PVDC | $\leq 0.1$ |
| PP film | no | $AlO_x$ | PVDC | 0.32 |
| PP film | yes | $AlO_x$ | PVDC | 0.028 |

What is claimed is:

1. A sample assembly comprising:

a plastic container having an open end, a closed end, an inner surface and an outer surface; and a multi-layer barrier coating applied to the outer surface of said container, said coating having a first layer applied to the outer surface of said container comprising a plasma-deposited inorganic material of aluminum oxide and a second layer applied to said first layer, comprising a parylene polymer or vinylidene chloride-acrylonitrile-methyl methacrylate-methyl acrylate-acrylic acid polymer.

2. The assembly of claim 1 wherein said second layer is a parylene polymer.

3. The assembly of claim 2 wherein said parylene polymer is parylene N, parylene C or parylene D.

* * * * *